US 6,384,910 B2

(12) United States Patent
Vaez-Iravani et al.

(10) Patent No.: US 6,384,910 B2
(45) Date of Patent: May 7, 2002

(54) SAMPLE INSPECTION SYSTEM

(75) Inventors: Mehdi Vaez-Iravani, Santa Clara; Stanley Stokowski, Danville; Guoheng Zhao, Sunnyvale, all of CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 09/745,492

(22) Filed: Dec. 21, 2000

Related U.S. Application Data

(62) Division of application No. 08/933,771, filed on Sep. 19, 1997, now Pat. No. 6,201,601.

(51) Int. Cl.$^7$ ............................................. G01N 21/88
(52) U.S. Cl. ................................ 356/237.2; 356/237.4; 356/623
(58) Field of Search .................... 356/237.1, 237.2, 356/237.3, 237.4, 237.5, 601, 602, 612, 614, 622, 623, 73; 250/559.31, 559.29

(56) References Cited

U.S. PATENT DOCUMENTS

| 4,449,818 A | | 5/1984 | Yamaguchi |
| 4,558,949 A | * | 12/1985 | Uehara et al. ............... 356/375 |
| 4,589,773 A | * | 5/1986 | Ido et al. ..................... 356/371 |
| 4,794,265 A | | 12/1988 | Quackenbos et al. |
| 4,893,932 A | | 1/1990 | Knollenberg |
| 4,898,471 A | | 2/1990 | Stonestrom et al. |
| 4,929,845 A | | 5/1990 | Amir et al. |
| 5,058,982 A | | 10/1991 | Katzir |
| 5,125,741 A | * | 6/1992 | Okada et al. ................ 356/371 |
| 5,189,481 A | * | 2/1993 | Jann et al. ..................... 356/73 |
| 5,389,794 A | | 2/1995 | Allen et al. |
| 5,416,594 A | | 5/1995 | Gross et al. |
| 5,424,838 A | | 6/1995 | Siu |
| 5,530,550 A | | 6/1996 | Nikoonahad et al. |
| 5,650,614 A | | 7/1997 | Yasutake et al. |
| 5,672,885 A | * | 9/1997 | Allen et al. .................. 356/373 |
| 5,712,701 A | * | 1/1998 | Clementi et al. ........... 356/237 |
| 5,798,829 A | | 8/1998 | Vaez-Iravani |
| 5,929,983 A | * | 7/1999 | Lu ............................... 356/138 |

FOREIGN PATENT DOCUMENTS

| DE | 4123916 | 1/1992 |
| EP | 0624787 | 11/1994 |
| WO | WO97/12226 | 4/1997 |
| WO | WO97/33158 | 9/1997 |

OTHER PUBLICATIONS

"Surface Inspection System for Estimation of Wafer," Y. Yatsugake et al., *Hitachi Electronics Engineering Technical Report*, vol. 11, Jan. 1996, pp. 21–26.
Figure, Hitachi Electronics Engineering Co., Ltd., presented by Etsuro Morita of Mitsubishi Materials Silicon Corp. in a presentation entitled "Exploration of COP and COP Defect Crystal Originated 'Particles'," at the 6$^{th}$ International Workshop on 300 Millimeter Wafers on Dec. 5, 1996, in Makuhari, Japan.
Partial European Search Report dated Oct. 18, 2000.

* cited by examiner

*Primary Examiner*—Hoa Q. Pham
(74) *Attorney, Agent, or Firm*—James S. Hsue; Skjerven Morrill MacPherson, LLP

(57) ABSTRACT

A curved mirrored surface is used to collect radiation scattered by a sample surface and originating from a normal illumination beam and an oblique illumination beam. The collected radiation is focused to a detector. Scattered radiation originating from the normal and oblique illumination beams may be distinguished by employing radiation at two different wavelengths, by intentionally introducing an offset between the spots illuminated by the two beams or by switching the normal and oblique illumination beams on and off alternately. Beam position error caused by change in sample height may be corrected by detecting specular reflection of an oblique illumination beam and changing the direction of illumination in response thereto. Butterfly-shaped spatial filters may be used in conjunction with curved mirror radiation collectors to restrict detection to certain azimuthal angles.

17 Claims, 8 Drawing Sheets

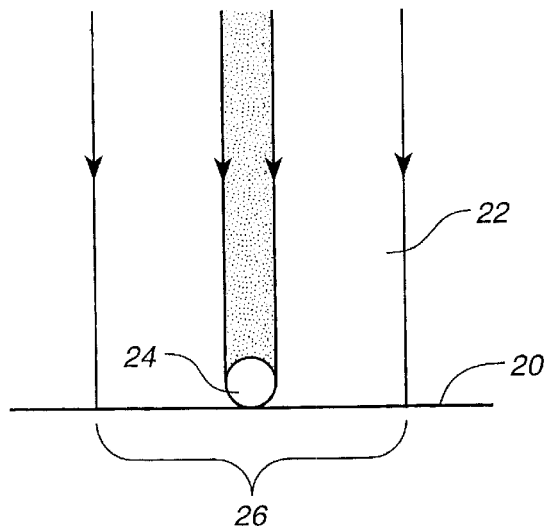
FIG._1A
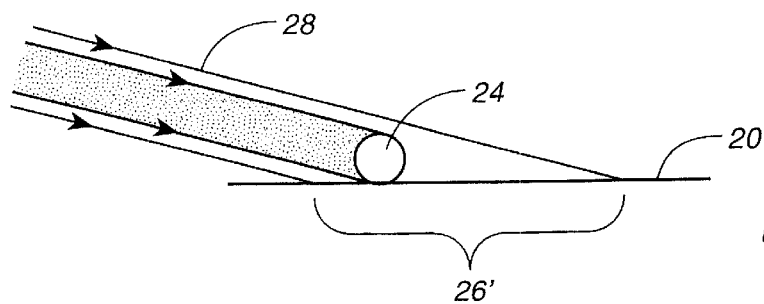
FIG._1B
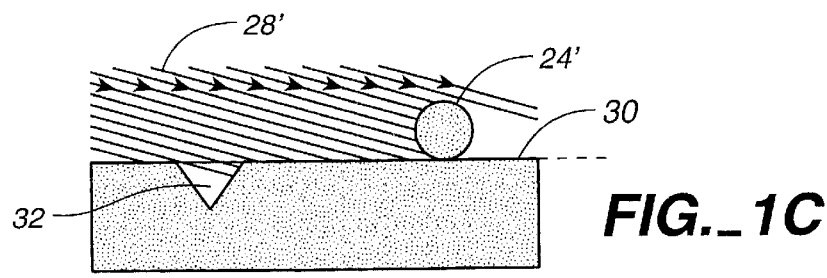
FIG._1C
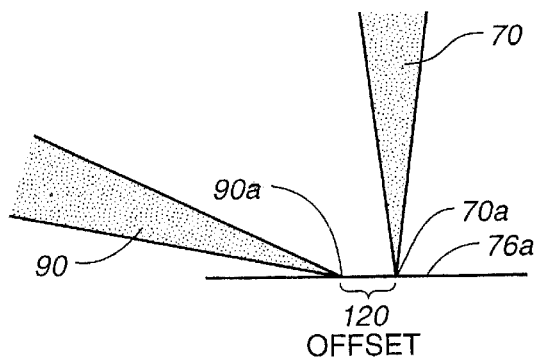
FIG._3

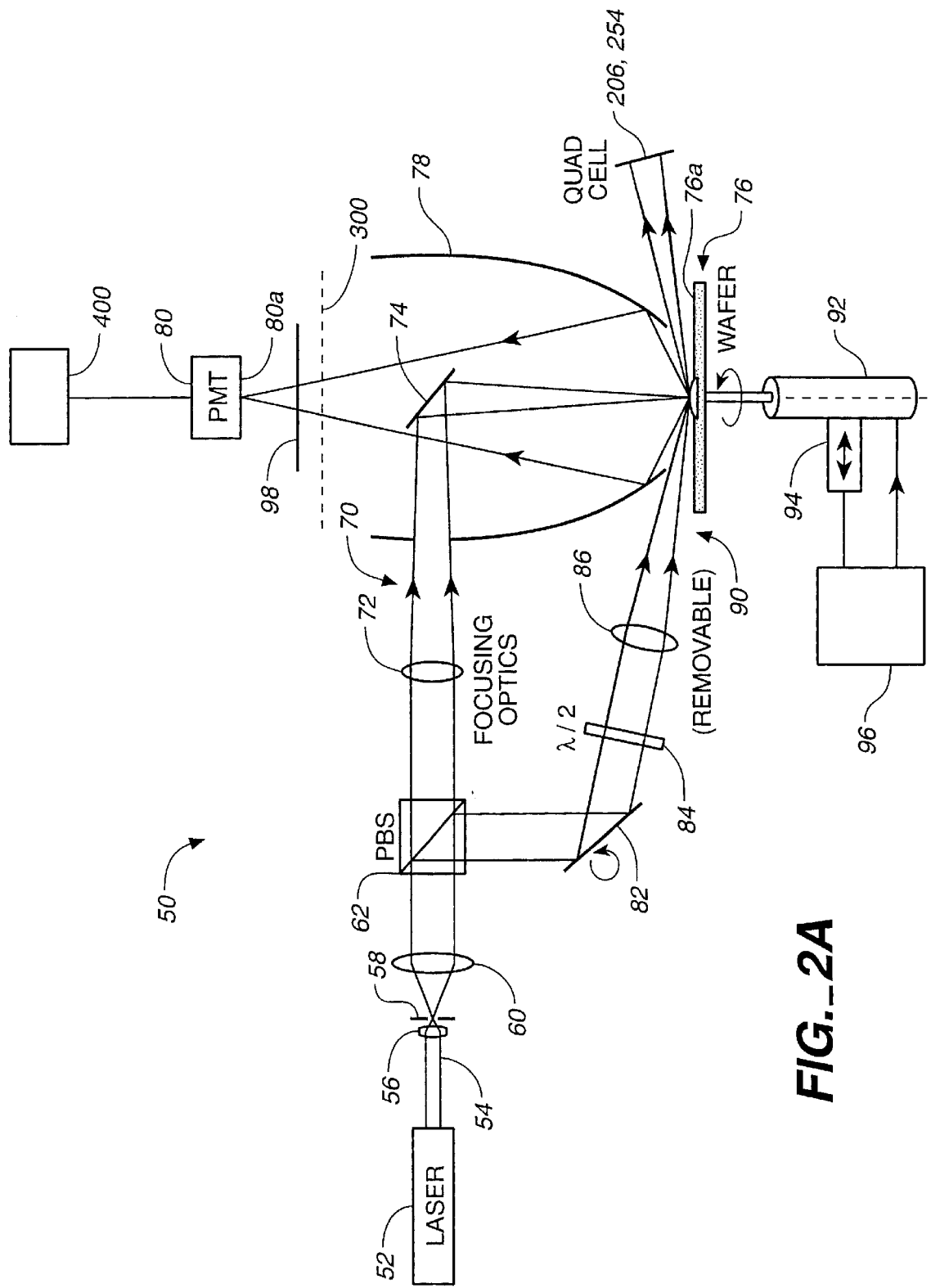
FIG._2A

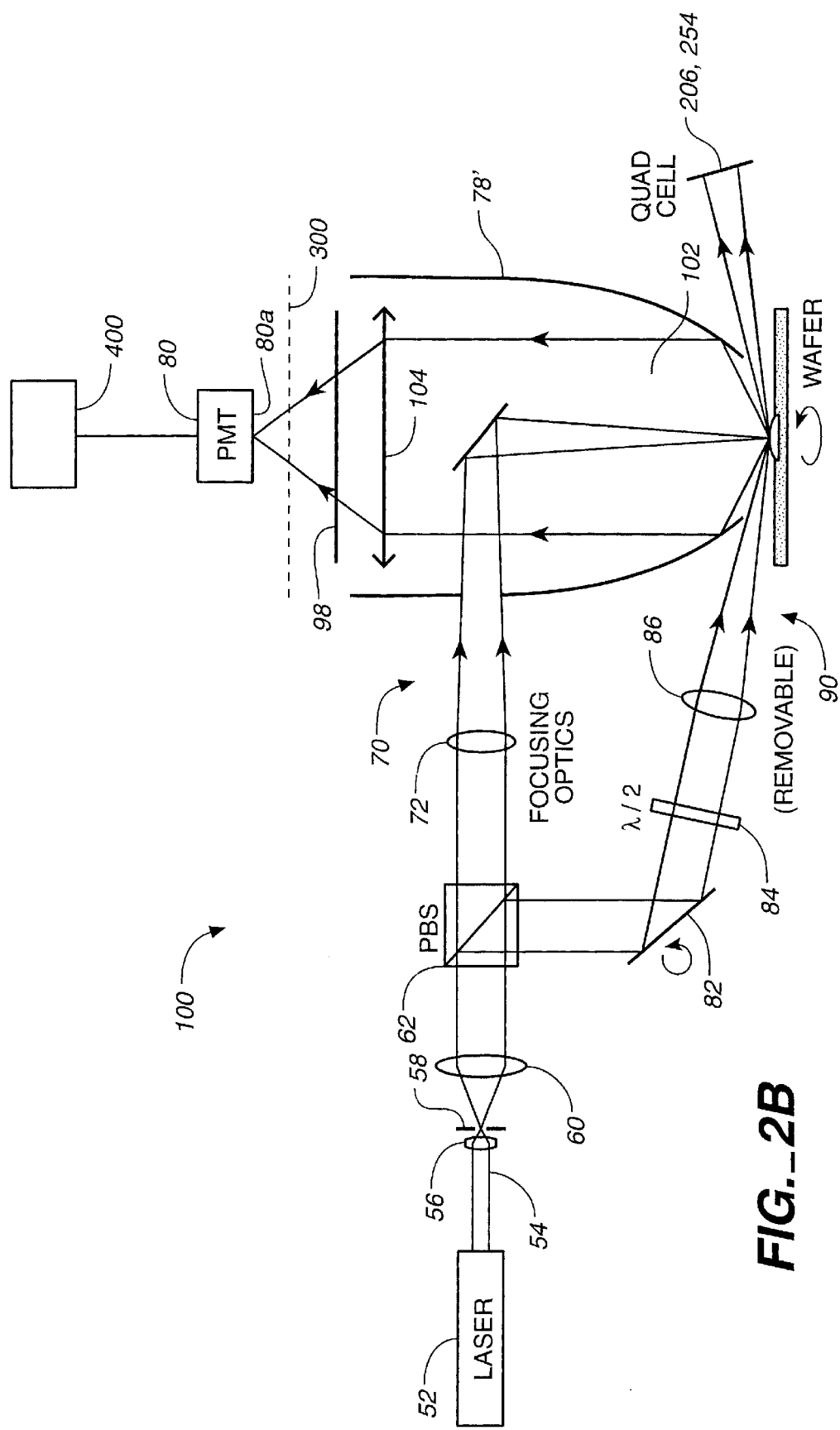
FIG._2B

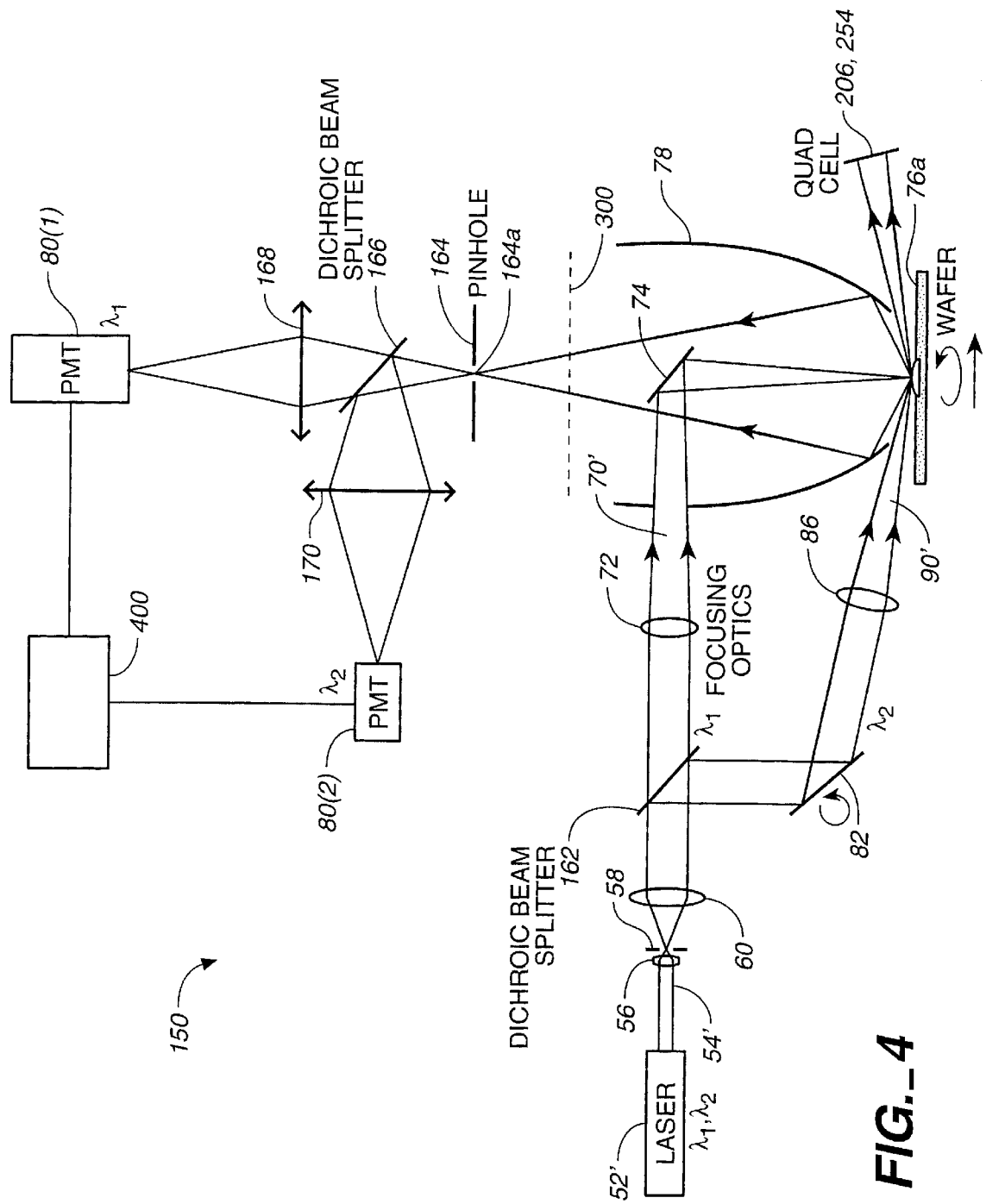
FIG._4

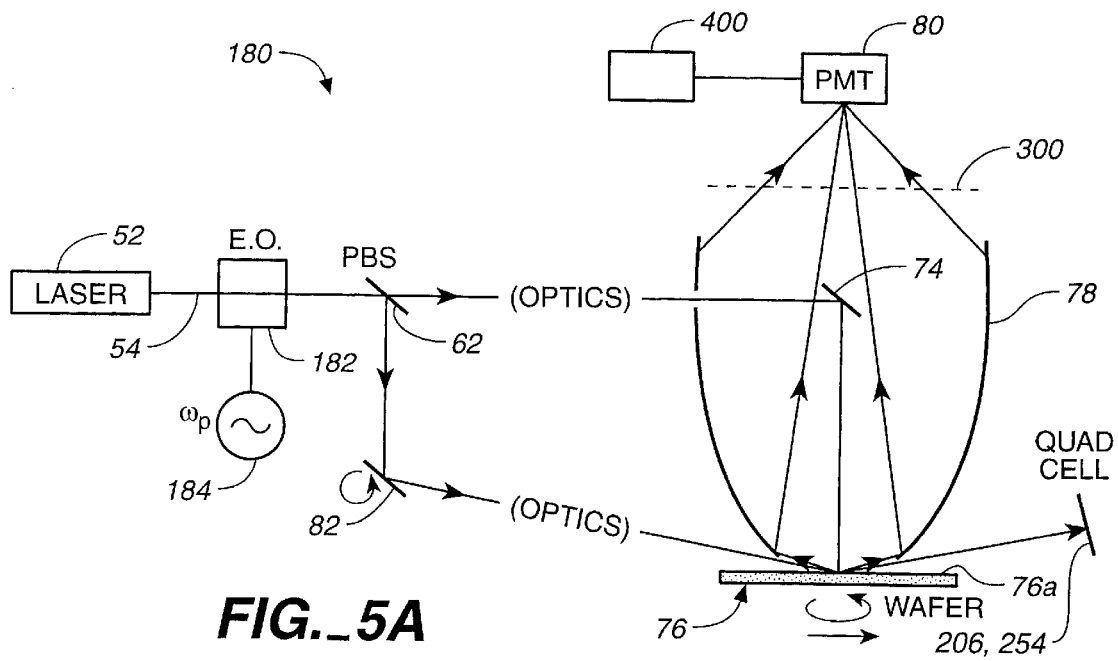
FIG._5A
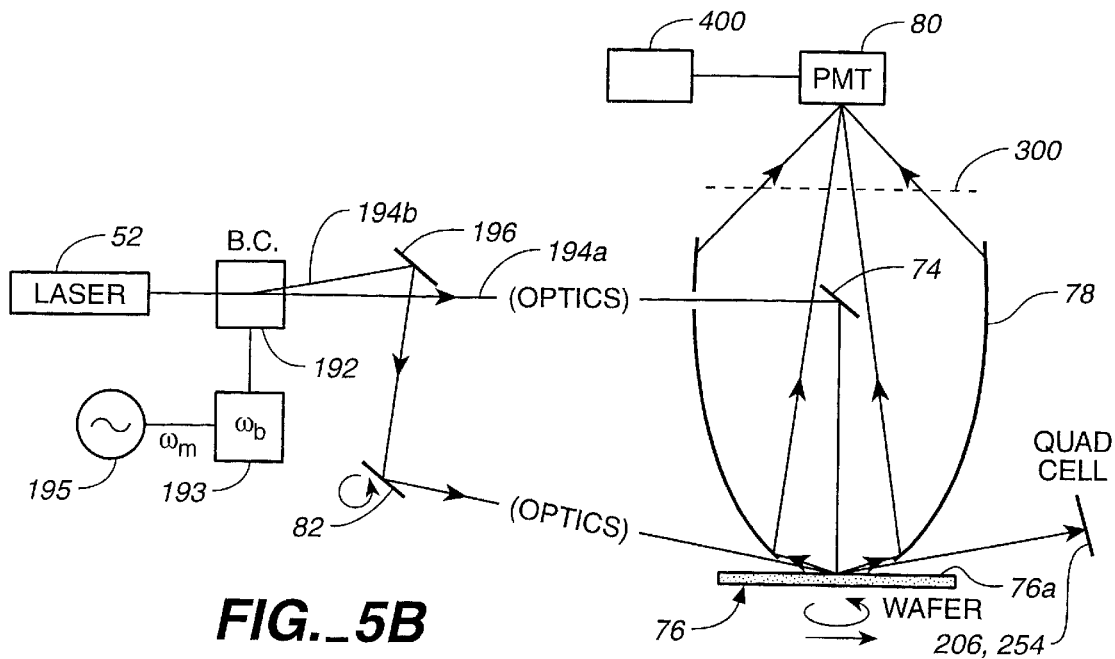
FIG._5B

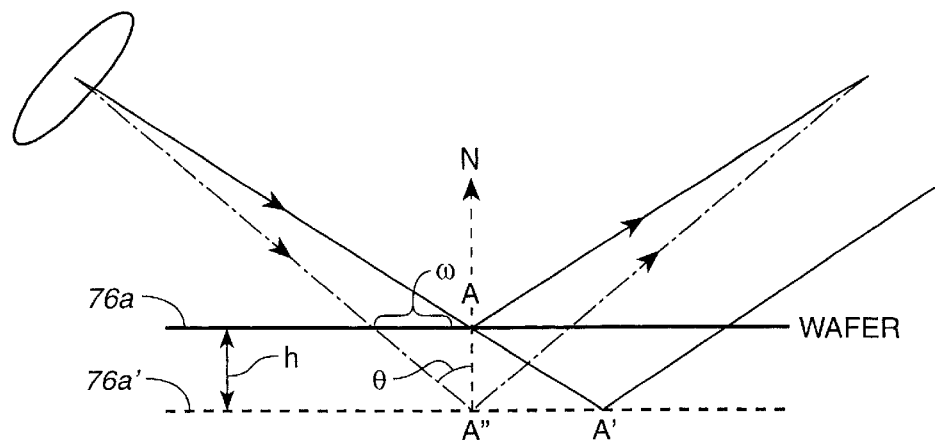
FIG._6
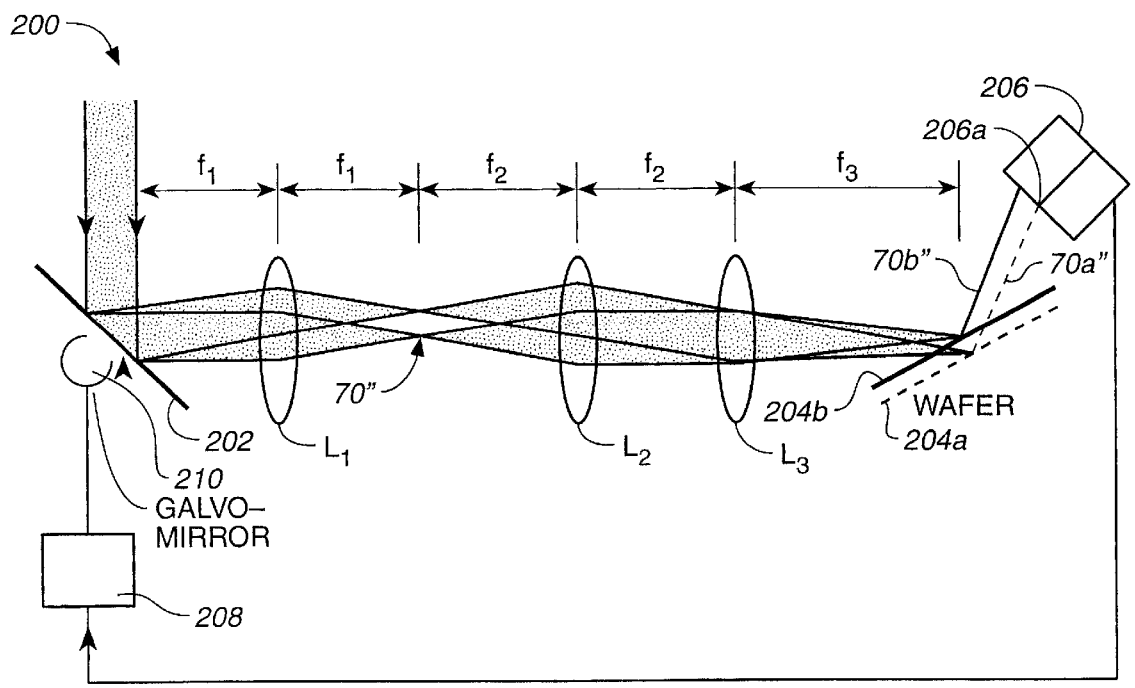
FIG._7

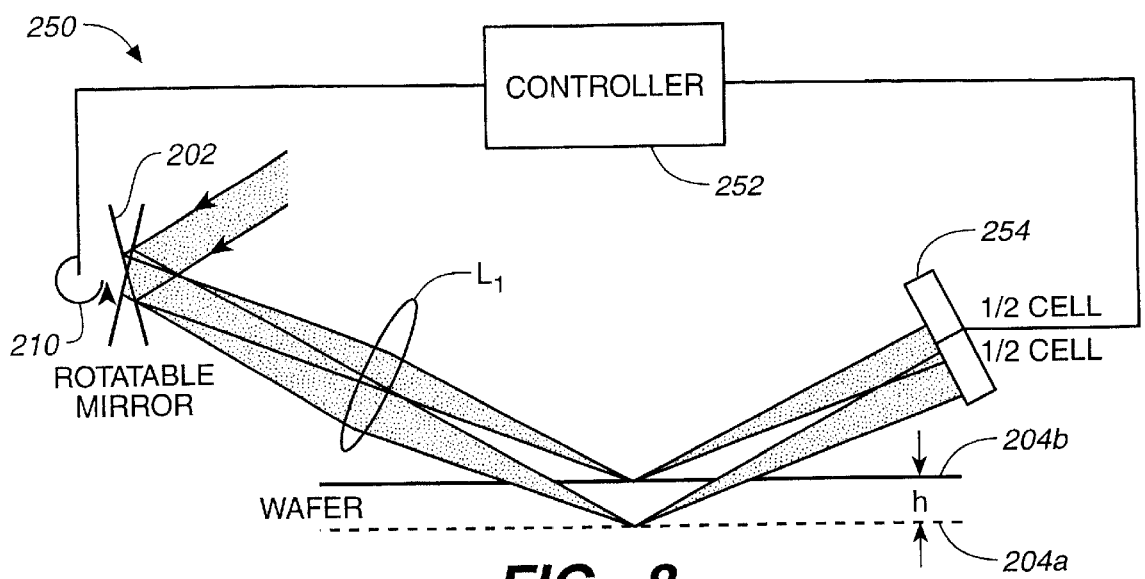
FIG._8
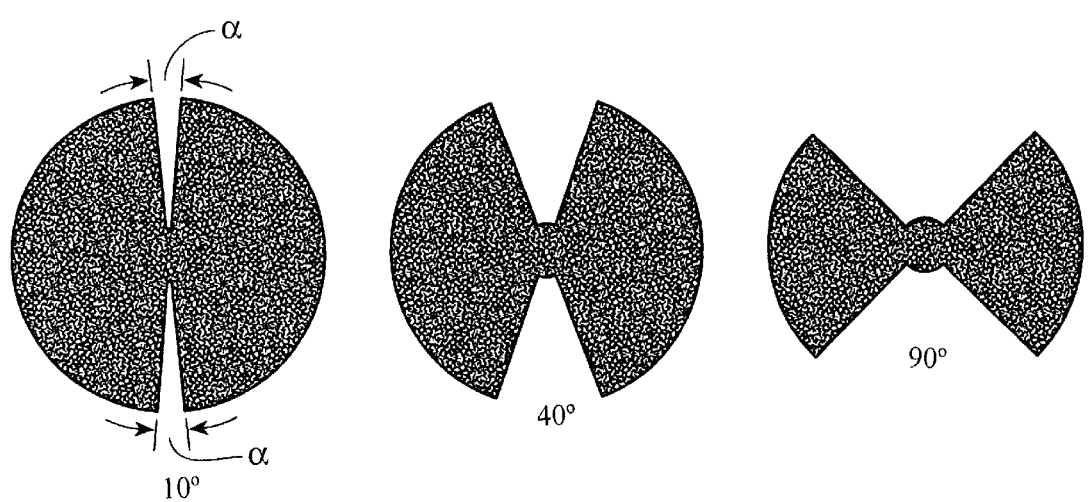
FIG._9A (10°)    FIG._9C (40°)    FIG._9E (90°)
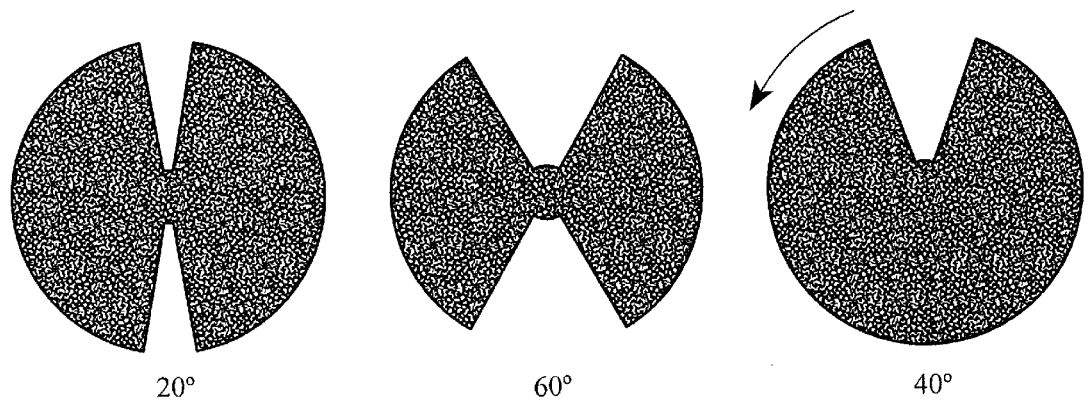
FIG._9B (20°)    FIG._9D (60°)    FIG._9F (40°)

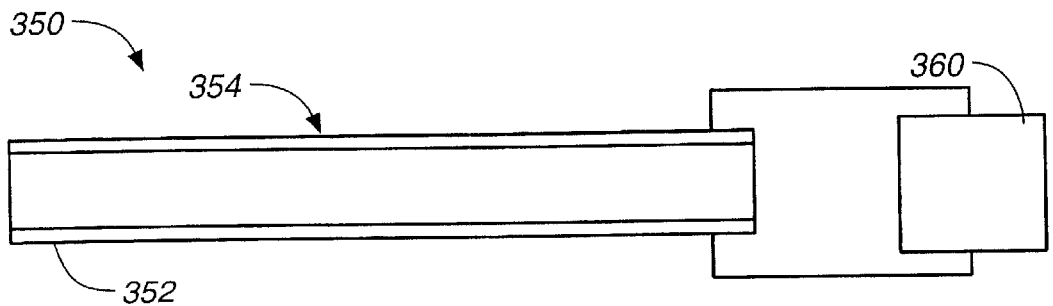
FIG._10A
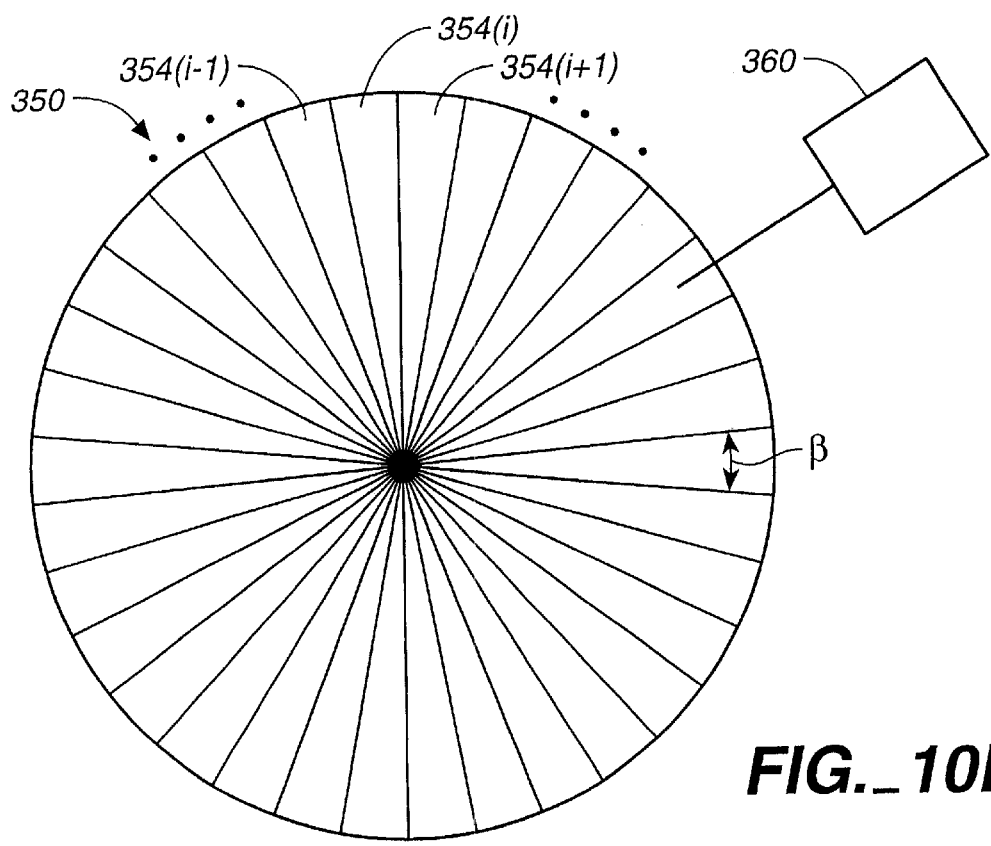
FIG._10B

SAMPLE INSPECTION SYSTEM

This application is a divisional application of U.S. patent application Ser. No. 08/933,771 filed Sep. 19, 1997, now U.S. Pat. No. 6,201,601.

BACKGROUND OF THE INVENTION

This invention relates in general to sample inspection systems and, in particular, to an improved inspection system with good sensitivity for particles as well as crystal-originated-particles (COPs). COPs are surface breaking defects in semiconductor wafers which have been classified as particles due to inability of conventional inspection systems to distinguish them from real particles.

Systems for inspecting unpatterned wafers or bare wafers have been proposed. See for example, PCT Patent Application No. PCT/US96/15354, filed on Sep. 25, 1996, entitled "Improved System for Surface Inspection." Systems such as those described in the above-referenced application are useful for many applications, including the inspection of bare or unpatterned semiconductor wafers. Nevertheless, it may be desirable to provide improved sample inspection tools which may be used for inspecting not only bare or unpatterned wafers but also rough films. Another issue which has great significance in wafer inspection is that of COPS. These are surface-breaking defects in the wafer. According to some opinions in the wafer inspection community, such defects can cause potential detriments to the performance of semiconductor chips made from wafers with such defects. It is, therefore, desirable to provide an improved sample inspection system capable of detecting COPs and distinguishing COPs from particles.

SUMMARY OF THE INVENTION

This invention is based on the observation that anomaly detection employing an oblique illumination beam is much more sensitive to particles than to COPs, whereas in anomaly detection employing an illumination beam normal to the surface, the difference in sensitivity to surface particles and COPs is not as pronounced. Anomaly detection employing both an oblique illumination beam and a normal illumination beam can then be used to distinguish between particles and COPs.

One aspect of the invention is directed towards an optical system for detecting anomalies of a sample, comprising first means for directing a first beam of radiation along a first path onto a surface of the sample; second means for directing a second beam of radiation along a second path onto a surface of the sample and a first detector. The system further comprises means including a mirrored surface for receiving scattered radiation from the sample surface and originating from the first and second beams and for focusing the scattered radiation to said first detector.

Another aspect of the invention is directed towards an optical system for detecting anomalies of a sample, comprising first means for directing a first beam of radiation along a first path onto a surface of a sample; second means for directing a second beam of radiation along a second path onto a surface of the sample, said first and second beams producing respectively a first and a second illuminated spot on the sample surface, said first and second illuminated spots separated by an offset. The system further comprises a detector and means for receiving scattered radiation from the first and second illuminated spots and for focusing the scattered radiation to said detector.

One more aspect of the invention is directed towards an optical system for detecting anomalies of a sample, comprising a source supplying a beam of radiation at a first and a second wavelength; and means for converting the radiation beam supplied by the source into a first beam at a first wavelength along a first path and a second beam at a second wavelength along a second path onto a surface of a sample. The system further comprises a first detector detecting radiation at the first wavelength and a second detector detecting radiation at the second wavelength; and means for receiving scattered radiation from the sample surface and originating from the first and second beams and for focusing the scattered radiation to said detectors.

Yet another aspect of the invention is directed towards an optical system for detecting anomalies of a sample, comprising a source supplying a radiation beam; a switch that causes the radiation beam from the source to be transmitted towards the sample surface alternately along a first path and a second path; a detector and means for receiving scattered radiation from the sample surface and originating from the beam along the first and second paths and for focusing the scattered radiation to said detector.

Another aspect of the invention is directed towards an optical system for detecting anomalies of a sample, comprising means for directing at least one beam of radiation along a path onto a spot on a surface of the sample; a first detector and means for receiving scattered radiation from the sample surface and originating from the at least one beam and for focusing the scattered radiation to said first detector for sensing anomalies. The system further comprises a second, position sensitive, detector detecting a specular reflection of said at least one beam in order to detect any change in height of the surface at a spot; and means for altering the path of the at least one beam in response to the detected change in height of the surface of the spot to reduce position error of the spot caused by change in height of the surface of the spot.

Still another aspect of the invention is directed towards an optical system for detecting anomalies of a sample, comprising means for directing at least one beam of radiation along a path onto a spot on a surface of the sample; a first detector and means for collecting scattered radiation from the sample surface and originating from the at least one beam and for conveying the scattered radiation to said first detector for sensing anomalies. The system further comprises a spatial filter between the first detector and the collecting and conveying means blocking scattered radiation towards the detector except for at least one area having a wedge shape.

One more aspect of the invention is directed towards an optical method for detecting anomalies of a sample, comprising directing a first beam of radiation along a first path onto a surface of the sample; directing a second beam of radiation along a second path onto a sample of the surface; employing a mirrored surface for receiving scattered radiation from the sample surface and originating from the first and second beams and focusing the scattered radiation to a first detector.

Yet another aspect of the invention is directed towards an optical method for detecting anomalies of a sample, comprising directing a first beam of radiation along a first path onto a surface of the sample; directing a second beam of radiation along a second path onto a surface of the sample, said first and second beams producing respectively a first and a second illuminated spot on the sample surface, said first and second illuminated spots separated by an offset. The method further comprises receiving scattered radiation from the first and second illuminated spots and for focusing the scattered radiation to a detector.

An additional aspect of the invention is directed towards an optical method for detecting anomalies of a sample, comprising supplying a beam of radiation of a first and a second wavelength; converting the radiation beam into a first beam at a first wavelength along a first path and a second beam at a second wavelength along a second path, said two beams directed towards a surface of the sample. The method further comprises collecting scattered radiation from the sample surface and originating from the first and second beams, focusing the collected scattered radiation to one or more detectors, and detecting radiation at the first and second wavelengths by means of said detectors.

Yet another aspect of the invention is directed towards an optical method for detecting anomalies of a sample, comprising supplying a radiation beam, switching alternately the radiation beam between a first and a second path towards a surface of the sample, receiving scattered radiation from the sample surface and originating from the beam along the first and second paths, and focusing the scattered radiation to a detector.

Another aspect of the invention is directed towards an optical method for detecting anomalies of a sample, comprising directing at least one beam of radiation along a path onto a spot on the surface of the sample; collecting scattered radiation from the sample surface and originating from the at least one beam, and focusing the collected scattered radiation to a first detector for sensing anomalies. The method further comprises detecting a specular reflection of said at least one beam in order to detect any change in height of the surface at the spot and altering the path of the at least one beam in response to the detected change in height of the surface of the spot to reduce position error of the spot caused by change in height of the surface of the spot.

One more aspect of the invention is directed towards an optical method for detecting anomalies of a sample, comprising directing at least one beam of radiation along a path onto a spot on a surface of the sample; collecting scattered radiation from the sample surface and originating from the at least one beam, conveying the scattered radiation to a first detector for sensing anomalies, and blocking scattered radiation towards the detector except for at least one area having a wedge shape.

Still another aspect of the invention is directed towards an optical system for detecting anomalies of a sample, comprising means for directing a beam of radiation along a path at an oblique angle to a surface of the sample; a detector and means including a curved mirrored surface for collecting scattered radiation from the sample surface and originating from the beam and for focusing the scattered radiation to said detector.

One more aspect of the invention is directed towards an optical method for detecting anomalies of a sample, comprising directing a beam of radiation along a path at an oblique angle to a surface of the sample; providing a curved mirrored surface to collect scattered radiation from the sample surface and originating from the beam, and focusing the scattered radiation from the mirrored surface to a detector to detect anomalies of the sample.

BRIEF DESCRIPTION OF THE DRAWINGS

FIGS. 1A, 1B and 1C are schematic views of normal or oblique illumination beams illuminating a surface with a particle thereon useful for illustrating the invention.

FIG. 2A is a schematic view of a sample inspection system employing an ellipsoidal mirror for illustrating one embodiment of the invention.

FIG. 2B is a schematic view of a sample inspection system employing a paraboloidal mirror to illustrate another embodiment of the invention.

FIG. 3 is an exploded simplified view of a portion of the system of FIG. 2A or FIG. 2B to illustrate another aspect of the invention.

FIG. 4 is a schematic view of a sample inspection system employing two different wavelengths for illumination to illustrate yet another embodiment of the invention.

FIGS. 5A and 5B are schematic views of sample inspection systems illustrating two different embodiments employing switches for switching a radiation beam between a normal illumination path and an oblique illumination path to illustrate yet another aspect of the invention.

FIG. 6 is a schematic view of a beam illuminating a semiconductor wafer surface to illustrate the effect of a change in height of a wafer on the position of the spot illuminated by beam.

FIG. 7 is a schematic view of a portion of a sample inspection system inspecting a semiconductor wafer, employing three lenses, where the direction of the illumination beam is altered to reduce the error in the position of the illuminated spot caused by the change in height of the wafer.

FIG. 8 is a schematic view of a portion of a sample inspection system employing only one lens to compensate for a change in height of the wafer.

FIGS. 9A–9F are schematic views of six different spatial filters useful for detecting anomalies of samples.

FIG. 10A is a simplified partially schematic and partially cross-sectional view of a programmable spatial filter employing a layer of liquid crystal material sandwiched between an electrode and an array of electrodes in the shape of sectors of a circle and means for applying a potential difference across at least one sector in the array and the other electrode, so that the portion of the liquid crystal layer adjacent to the at least one sector is controlled to be radiation transparent or scattering.

FIG. 10B is a top view of the filter of FIG. 10A.

For simplicity in description, identical components are labelled by the same numerals in this application.

DETAILED DESCRIPTION OF THE PREFERRED EMBODIMENT

FIG. 1A is a schematic view of a surface 20 of a sample to be inspected and an illumination beam 22 directed in a direction normal to surface 20 to illuminate the surface and a particle 24 on the surface. Thus, the illumination beam 22 illuminates an area or spot 26 of surface 20 and a detection system (not shown) detects light scattered by particle 24 and by portion or spot 26 of the surface 20. The ratio of the photon flux received by the detector from particle 24 to that from spot 26 indicates the sensitivity of the system to particle detection.

If an illumination beam 28 directed at an oblique angle to surface 20 is used to illuminate spot 26' and particle 24 instead, as shown in FIG. 1B, from a comparison between FIGS. 1A and 1B, it will be evident that the ratio of the photon flux from the particle 24 to that from the illuminated spot will be greater in the case of the oblique illumination in FIG. 1B compared to that in FIG. 1A. Therefore, for the same throughput (spots 26, 26' having the same area), the sensitivity of the oblique incidence beam in detecting small particles is superior and is the method of choice in the detection of small particles.

FIG. 1C illustrates an oblique beam 28' illuminating a surface 30 having a pit 32 and particle 24' thereon. As can be seen from FIG. 1C, even though the pit 32 is of comparable size to particle 24, it will scatter a much smaller amount of photon flux compared to particle 24 from oblique beam 28'. On the other hand, if the pit 32 and particle 24 are illuminated by a beam such as 22 directed in a direction normal to surface 30, pit 32 and particle 24 would cause comparable amount of photon flux scattering. Almost regardless of the exact shape or orientation of COPs and particles, anomaly detection employing oblique illumination is much more sensitive to particles than COPs. In the case of anomaly detection with normal illumination, however, the differentiation between particles and COPs is less pronounced. Therefore, by means of a simultaneous, or sequential, comparison of feature signatures due to normal and oblique illumination will reveal whether the feature is a particle or a COP.

Azimuthal collection angle is defined as the angle made by the collection direction to the direction of oblique illumination when viewed from the top. By employing oblique illumination, together with a judicious choice of the azimuthal collection angle, rough films can be inspected with good sensitivity, such as when a spatial filter shown in any of FIGS. 9A–9F, 10A and 10B is used in any one of the embodiments as shown in FIGS. 2A, 2B, 3, 4, 5A and 5B, as explained below. By retaining the normal illumination beam for anomaly detection, all of the advantageous attributes of the system described in PCT Patent Application No. PCT/US96/15354 noted above, are retained, including its uniform scratch sensitivity and the possibility of adding a bright-field channel as described in PCT Patent Application No. PCT/US97/04134, filed Mar. 5, 1997, entitled "Single Laser Bright Field and Dark Field System for Detecting Anomalies of a Sample."

Scanning a sample surface with oblique and normal illumination beams can be implemented in a number of ways. FIG. 2A is a schematic view of a sample inspection system to illustrate a general set up for implementing anomaly detection using both normal and oblique illumination beams. A radiation source that provides radiation at one or more wavelengths in a wide electromagnetic spectrum (including but not limited to ultraviolet, visible, infrared) may be used, such as a laser 52 providing a laser beam 54. A lens 56 focuses the beam 54 through a spatial filter 58 and lens 60 collimates the beam and conveys it to a polarizing beamsplitter 62. Beamsplitter 62 passes a first polarized component to the normal illumination channel and a second polarized component to the oblique illumination channel, where the first and second components are orthogonal. In the normal illumination channel 70, the first polarized component is focused by optics 72 and reflected by mirror 74 towards a sample surface 76a of a semiconductor wafer 76. The radiation scattered by surface 76a is collected and focused by an ellipsoidal mirror 78 to a photomultiplier tube 80.

In the oblique illumination channel 90, the second polarized component is reflected by beamsplitter 62 to a mirror 82 which reflects such beam through a half-wave plate 84 and focused by optics 86 to surface 76a. Radiation originating from the oblique illumination beam in the oblique channel 90 and scattered by surface 76a is collected by an ellipsoidal mirror and focused to photomultiplier tube 80. Photomultiplier tube 80 has a pinhole entrance 80a. The pinhole 80a and the illuminated spot (from the normal and oblique illumination channels on surface 76a) are preferably at the foci of the ellipsoidal mirror 78.

Wafer 76 is rotated by a motor 92 which is also moved linearly by transducer 94, and both movements are controlled by a controller 96, so that the normal and oblique illumination beams in channels 70 and 90 scan surface 76a along a spiral scan to cover the entire surface.

Instead of using an ellipsoidal mirror to collect the light scattered by surface 76a, it is also possible to use other curved mirrors, such as a paraboloidal mirror 78' as shown in system 100 of FIG. 2B. The paraboloidal mirror 78' collimates the scattered radiation from surface 76a into a collimated beam 102 and the collimated beam 102 is then focused by an objective 104 and through an analyzer 98 to the photomultiplier tube 80. Aside from such difference, the sample inspection system 100 is exactly the same as system 50 of FIG. 2A. Curved mirrored surfaces having shapes other than ellipsoidal or paraboloidal shapes may also be used; preferably, each of such curved mirrored surfaces has an axis of symmetry substantially coaxial with the path of the normal illumination path, and defines an input aperture for receiving scattered radiation. All such variations are within the scope of the invention. For simplicity, the motor, transducer and control for moving the semiconductor wafer has been omitted from FIG. 2B and from FIGS. 4, 5A, 5B described below.

The general arrangements shown in FIGS. 2A and 2B can be implemented in different embodiments. Thus, in one arrangement referred to below as the "GO and RETURN" option, a half-wave plate (not shown) is added between laser 52 and lens 56 in FIGS. 2A and 2B so that the polarization of the light reaching the beamsplitter 62 can be switched between P and S. Thus, during the Go cycle, the beamsplitter 62 passes radiation only into the normal channel 70 and no radiation will be directed towards the oblique channel 90. Conversely, during the RETURN cycle, beamsplitter 62 passes radiation only into the oblique channel 90 and no radiation will be directed through the normal channel 70. During the GO cycle, only the normal illumination beam 70 is in operation, so that the light collected by detector 80 is recorded as that from normal illumination. This is performed for the entire surface 76a where motor 92, transducer 94 and control 96 are operated so that the normal illumination beam 70 scans the entire surface 76a along a spiral scan path.

After the surface 76a has been scanned using normal illumination, the half-wave plate between laser 52 and lens 56 causes radiation from laser 52 to be directed only along the oblique channel 90 and the scanning sequence by means of motor 92, transducer 94 and control 96 is reversed and data at detector 80 is recorded in a RETURN cycle. As long as the forward scan in the GO cycle and the reverse scan in the RETURN cycle are exactly registered, the data set collected during the GO cycle and that collected during the return cycle may be compared to provide information concerning the nature of the defects detected. Instead of using a half-wave plate and a polarizing beamsplitter as in FIG. 2A, the above-described operation may also be performed by replacing such components with a removable mirror placed in the position of beamsplitter 62. If the mirror is not present, the radiation beam from laser 52 is directed along the normal channel 70. When the mirror is present, the beam is then directed along the oblique channel 90. Such mirror should be accurately positioned to ensure exact registration of the two scans during the GO and RETURN cycles. While simple, the above-described GO and RETURN option requires extra time expended in the RETURN cycle.

The normal illumination beam 70 illuminates a spot on surface 76a. The oblique illumination beam 90 also illuminates a spot on the surface 76a. In order for comparison of data collected during the two cycles to be meaningful, the two illuminated spots should have the same shape. Thus, if beam 90 has a circular cross-section, it would illuminate an elliptical spot on the surface. In one embodiment, focusing optics 72 comprises a cylindrical lens so that beam 70 has an elliptical cross-section and illuminates also an elliptical spot on surface 76a.

To avoid having to scan surface 76a twice, it is possible to intentionally introduce a small offset between the illuminated spot 70a from normal illumination beam 70 (referred to herein as "normal illumination spot" for simplicity) and the illuminated spot 90a from oblique illumination beam 90 (referred to herein as "oblique illumination spot" for simplicity) as illustrated in FIG. 3. FIG. 3 is an enlarged view of surface 76a and the normal and oblique illumination beams 70, 90 to illustrate an offset 120 between the normal and oblique illumination spots 70a, 90a. In reference to FIGS. 2A, 2B, radiation scattered from the two spots 70a, 90a would be detected at different times and would be distinguished.

The method illustrated in FIG. 3 causes a reduction in system resolution and increased background scattering due to the presence of both spots. In other words, in order that radiation scattered from both spots separated by an offset would be focused through pinhole 80a, the pinhole should be somewhat enlarged in the direction of the offset. As a consequence, detector 80 will sense an increased background scattering due to the enlargement of the pinhole 80a. Since the background is due to both beams whereas the particle scattered radiation is due to one or the other spot, the signal-to-noise ratio is decreased. Preferably, the offset is not greater than three times the spatial extent, or less than the spatial extent, of the point spread function of either the normal or oblique illumination beam. The method illustrated in FIG. 3, however, is advantageous since throughput is not adversely affected compared to that described in PCT Application No. PCT/US96/15354 and the Censor ANS series of inspection systems from KLA-Tencor Corporation of San Jose, Calif., the assignee of this application.

FIG. 4 is a schematic view of a sample inspection system employing a normal illumination beam comprising radiation at a first wavelength $\lambda_1$ and an oblique illumination beam of radiation of wavelength $\lambda_2$ to illustrate another embodiment of the invention. The laser 52 of FIGS. 2A, 2B may supply radiation at only one wavelength, such as 488 nm of argon. Laser 52' of FIG. 4 supplies radiation at at least two different wavelengths in beam 54', such as at 488 and 514 nm, instead of radiation of only one wavelength, Such beam is split by a dichroic beamsplitter 162 into a first beam at a first wavelength $\lambda_1$ (488 nm) and a second beam of wavelength $\lambda_2$ (514 nm), by passing radiation at wavelength $\lambda_1$ and reflecting radiation at wavelength $\lambda_2$, for example. After being focused by optics 72, beam 70' at wavelength $\lambda_1$ is reflected by mirror 74 towards surface 76a as the normal illumination beam. The reflected radiation of wavelength $\lambda_2$ at beamsplitter 162 is further reflected by mirror 82 and focused by optics 86 as the oblique illumination beam 90' to illuminate the surface. The optics in both the normal and oblique illumination paths are such that the normal and oblique illuminated spots substantially overlap with no offset there between. The radiation scattered by surface 76a retains the wavelength characteristics of the beams from which the radiation originate, so that the radiation scattered by the surface originating from normal illumination beam 70' can be separated from radiation scattered by the surface originating from oblique illumination beam 90'. Radiation scattered by surface 76a is again collected and focused by an ellipsoidal mirror 78 through a pinhole 164a of a spatial filter 164 to a dichroic beamsplitter 166. In the embodiment of FIG. 4, beamsplitter 166 passes the scattered radiation at wavelength $\lambda_1$ to detector 80(1) through a lens 168. Dichroic beamsplitter 166 reflects scattered radiation at wavelength $\lambda_2$ through a lens 170 to photomultiplier tube 80(2). Again, the mechanism for causing the wafer to rotate along a spiral path has been omitted from FIG. 4 for simplicity.

Instead of using a laser that provides radiation at a single wavelength, the laser source 52' should provide radiation at two distinct wavelengths. A commercially available multi-line laser source that may be used is the 2214–65-ML manufactured by Uniphase, San Jose, Calif. The amplitude stability of this laser at any given wavelength is around 3.5%. If such a laser is used, the scheme in FIG. 4 will be useful for applications such as bare silicon inspection but may have diminished particle detection sensitivity when used to scan rough films.

Yet another option for implementing the arrangements generally shown in FIGS. 2A and 2B is illustrated in FIGS. 5A and 5B. In such option, a radiation beam is switched between the normal and oblique illumination channels at a higher frequency than the data collection rate so that the data collected due to scattering from the normal illumination beam may be distinguished from data collected from scattering due to the oblique illumination channel. Thus as shown in FIG. 5A, an electro-optic modulator (e.g. a Pockels cell) 182 is placed between laser 52 and beamsplitter 62 to modulate the radiation beam 54 at the half-wave voltage. This results in the beam being either transmitted or reflected by the polarizing beamsplitter 62 at the drive frequency of modulator 182 as controlled by a control 184.

The electro-optic modulator may be replaced by a Bragg modulator 192 as shown in FIG. 5B, which may be turned on and off at a high frequency as controlled. Modulator 192 is powered by block 193 at frequency $\omega_b$. This block is turned on and off at a frequency $\omega_m$. In the off condition, a zero order beam 194a passes through the Bragg modulator 192, and becomes the normal illumination beam reflected to surface 76a by mirror 74. In the on condition, cell 192 generates a deflected first order beam 194b, which is reflected by mirrors 196, 82 to surface 76a. However, even though most of the energy from cell 192 is directed to the oblique first order beam, a weak zero order normal illumination beam is still maintained, so that the arrangement in FIG. 5B is not as good as that in FIG. 5A.

Preferably, the electro-optic modulator of FIG. 5A and the Bragg modulator of FIG. 5B are operated at a frequency higher than the data rate, and preferably, at a frequency at least about 3 or 5 times the data rate of tube 80. As in FIG. 4, the optics in both the normal and oblique illumination paths of FIGS. 5A, 5B are such that the normal and oblique illuminated spots substantially overlap with no offset there between. The arrangements in FIGS. 2A, 2B, 4, 5A, 5B are advantageous in that the same radiation collector 78 and detector 80 are used for detecting scattered light originating from the normal illumination beam as well as from the oblique illumination beam. Furthermore, by employing a curved surface that collects radiation that is scattered within the range of at least 25 to 70° from a normal direction to surface 76a and focusing the collected radiation to the detector, the arrangements of FIGS. 2A; 2B, 4, 5A, 5B maximize the sensitivity of detection.

In contrast to arrangements where multiple detectors are placed at different azimuthal collection angles relative to the oblique illumination beam, the arrangements of FIGS. 2A, 2B has superior sensitivity and is simpler in arrangement and operation, since there is no need to synchronize or correlate the different detection channels that would be required in a multiple detector arrangement. The ellipsoidal mirror 78 collects radiation scattered within the range of at least 25 to 70° from the normal direction to the surface which accounts for most of the radiation that is scattered by surface 76a from an oblique illumination beam, and that contains information useful for particle and COPs detection.

The three dimensional intensity distribution of scattered radiation from small particles on the surface when the surface is illuminated by a P-polarized illumination beam at or near a grazing angle to the surface has the shape of a toroid. In the case of large particles, higher scattered intensity is detected in the forward direction compared to other directions. For this reason, the curved mirror collectors of FIGS. 2A, 2B, 4, 5A, 5B are particularly advantageous for collecting the scattered radiation from small and large particles and directing the scattered radiation towards a detector. In the case of normal illumination, however, the intensity distribution of radiation scattered from small particles on surfaces is in the shape of a sphere. The collectors in FIGS. 2A, 2B, 4, 5A, 5B are also advantageous for collecting such scattered radiation. Preferably, the illumination angle of beam 90 is within the range of 45 to 85° from a normal direction to the sample surface, and preferably at 70 or 75°, which is close to the principal angle of silicon at 488 and 514 nm, and would allow the beam passage to be unhindered by the walls of the collector. By operating at this shallow angle, the particle photon flux is enhanced as illustrated in FIGS. 1A and 1B and the discrimination against the pits is substantial.

Beam Position Correction

A prerequisite for the comparison of signals generated by two detection channels for a given defect is the ability to place the two spots on the same location. In general, semiconductor wafers or other sample surfaces are not completely flat, nor do they have the same thickness. Such imperfections are of little concern for anomaly detection employing a normal incidence beam, as long as the wafer surface remains within the depth of focus. In the case of the oblique illumination beam, however, wafer-height variation will cause the beam position and hence the position of the illuminated spot to be incorrect. In FIG. 6, θ is the oblique incidence angle between the beam and a normal direction N to the wafer surface. Thus, as shown in FIG. 6, if the height of the wafer surface moves from the dotted line position 76a' to the solid line position 76a which is higher than the dotted line position by the height h, then the position of the illuminated spot on the wafer surface will be off by an error of w given by h.tan θ. one possible solution is to detect the change in height of the wafer at the illuminated spot and move the wafer in order to maintain the wafer at a constant height at the illuminated spot, as described in U.S. Pat. No. 5,530,550. In the embodiment described above, the wafer is rotated and translated to move along a spiral scan path so that it may be difficult to also correct the wafer height by moving the wafer while it is being rotated along such path. Another alternative is to move the light source and the detector when the height of the wafer changes so as to maintain a constant height between the light source and the detector on the one hand and the wafer surface at the illuminated spot on the other. This is obviously cumbersome and may be impractical. Another aspect of the invention is based on the observation that, by changing the direction of the illumination beam in response to a detected change in wafer height, it is possible to compensate for the change in wafer height to reduce beam position error caused thereby.

One scheme for implementing the above aspect is illustrated in FIG. 7. As shown in system 200 of FIG. 7, an illumination beam is reflected by a mirror 202 and focused through three lenses $L_1$, $L_2$, $L_3$ to the wafer surface 204a. The positions of the lenses are set in order to focus an oblique illumination beam 70" to wafer surface 204a in dotted line in FIG. 7. Then a quad cell (or other type of position sensitive detector) 206 is positioned so that the specular reflection 70a" of the beam 70" from surface 204 reaches the cell at the null or zero position 206a of the cell. As the wafer surface moves from position 204a to 204b shown in solid line in FIG. 7, such change in height of the wafer causes the specular reflection to move to position 70b", so that it reaches the cell 206 at a position on the cell offset from the null position 206a. Detector 206 may be constructed in the same manner as that described in U.S. Pat. No. 5,530,550. A position error signal output from detector 206 indicating the deviation from the null position in two orthogonal directions is sent by cell 206 to a control 208 which generates an error signal to a transducer 210 for rotating the mirror 202 so that the specular reflection 70b" also reaches the cell at the null position 206a. In other words, the direction of the illumination beam is altered until the specular reflection reaches the cell at null position, at which point control 208 applies no error signal to the transducer 210.

Instead of using three lenses, it is possible to employ a single lens as shown in FIG. 8, except that the correct placement of the illuminated spot on the wafer corresponds not to a null in the position sensing signal from the position sensitive detector, but corresponds to an output of the detector reduced by ½. This approach is shown in FIG. 8. Thus, controller 252 divides by 2 the amplitude of the position sensing signal at the output of quad cell detector 254 to derive a quotient signal and applies the quotient signal to transducer 210. The transducer 210 rotates the mirror by an amount proportional to the amplitude of the quotient signal. The new position of the specular reflection corresponds to the correct location of the spot. The new error signal is now the new reference.

The above described feature of reducing beam position error of the oblique illumination beam in reference to FIGS. 7 and 8 may be used in conjunction with any one of the inspection systems of FIGS. 2A, 2B, 3, 4, 5A and 5B, although only the quad cell (206 or 254) is shown in these figures.

Spatial Filter

In reference to the embodiments of FIGS. 2A, 2B, 4, 5A and 5B, it is noted that the radiation collection and detection schemes in such embodiments retain the information concerning the direction of scattering of the radiation from surface 76a relative to the oblique illumination channel 90 or 90'. This can be exploited for some applications such as rough surface inspection. This can be done by employing a spatial filter which blocks the scattered radiation collected by the curved mirrored surface towards the detector except for at least one area have a wedge shape. With respect to the normal illumination channel, there is no directional information since both the illumination and scattering are symmetrical about a normal to the surface. In other words, if the normal illumination channel is omitted in the embodiments of FIGS. 2A, 2B, 4, 5A and 5B, the curved mirrored collector 78 or 78' advantageously collects most of the radiation scattered within the toroidal intensity distribution caused by particle scattering to provide an inspection tool of high particle sensitivity. At the same time, the use of a curved mirrored collector retains the directional scattering information, where such information can be retrieved by employing a spatial filter as described below.

FIGS. 9A–9F illustrate six different embodiments of such spatial filters in the shape of butterflies each with two wings. The dark or shaded areas (wings) in these figures represent areas that are opaque to or scatters radiation, and the white or unshaded areas represent areas that transmit such radiation. The size(s) of the radiation transmissive (white or unshaded) area(s) are determined in each of the filters in FIGS. 9A–9F by the wedge angle α. Thus, in FIG. 9A, the wedge angle is 10°, whereas in FIG. 9B, it is 20°.

Thus, if the filter in FIG. 9B is placed at position 300 of FIG. 2A, 2B, 4, 5A or 5B where the 20° wedge-shaped area of radiation collection is centered at approximately 90° and 270° azimuthal collection angles relative to the oblique illumination direction, this has the effect of generating a combined output from two detectors, each with a collection angle of 20°, one detector placed to collect radiation between 80 to 100° azimuthal angles as in U.S. Pat. No. 4,898,471, and the other detector to collect radiation between 260 and 280° azimuthal angles. The detection scheme of U.S. Pat. No. 4,898,471 can be simulated by blocking out also the wedge area between 260 and 280 azimuthal angles. The arrangement of this application has the advantage over U.S. Pat. No. 4,898,471 of higher sensitivity since more of the scattered radiation is collected than in such patent, by means of the curved mirror collector 78, 78'. Furthermore, the azimuthal collection angle can be dynamically changed by programming the filter at position 300 in FIGS. 2A, 2B, 4, 5A, 5B without having to move any detectors, as described below.

It is possible to enlarge or reduce the solid angle of collection of the detector by changing α. It is also possible to alter the azimuthal angles of the wedge areas. These can be accomplished by having ready at hand a number of different filters with different wedge angles such as those shown in FIGS. 9A–9F, as well as filters with other wedge shaped radiation transmissive areas, and picking the desired filter and the desired position of the filter for use at position 300 in FIGS. 2A, 2B, 4, 5A, 5B. The spatial filters in FIGS. 9A–9E are all in the shape of butterflies with two wings, where the wings are opaque to or scatters radiation and the spaces between the wings transmit radiation between the mirrored surfaces and detector 80. In some applications, however, it may be desirable to employ a spatial filter of the shape shown in FIG. 9F having a single radiation transmissive wedge-shaped area. Obviously, spatial filters having any number of wedge-shaped areas that are radiation transmissive dispersed around a center at various different angles may also be used and are within the scope of the invention.

Instead of storing a number of filters having different wedge angles, different numbers of wedges and distributed in various configurations, it is possible to employ a programmable spatial filter where the opaque or scattering and transparent or transmissive areas may be altered. For example, the spatial filter may be constructed using corrugated material where the wedge angle α can be reduced by flattening the corrugated material. Or, two or more filters such as those in FIGS. 9A–9F may be superimposed upon one another to alter the opaque or scattering and transparent or transmissive areas.

Alternatively, a liquid crystal spatial filter may be advantageously used, one embodiment of which is shown in FIGS. 10A and 10B. A liquid crystal material can be made radiation transmissive or scattering by changing an electrical potential applied across the layer. The liquid crystal layer may be placed between a circular electrode 352 and an electrode array 354 in the shape of n sectors of a circle arranged around a center 356, where n is a positive integer. The sectors are shown in FIG. 10B which is a top view of one embodiment of filter 350 in FIG. 10A Adjacent electrode sectors 354(i) and 354(i+1), I ranging from 1 to n−1, are electrically insulated from each other.

Therefore, by applying appropriate electrical potentials across one or more of the sector electrodes 354(i), where (i) ranges from 1 to n, on one side, and electrode 352 on the other side, by means of voltage control 360, it is possible to programmably change the wedge angle α by increments equal to the wedge angle β of each of the sector electrodes 354(1) through 354(n). By applying the potentials across electrode 352 and the appropriate sector electrodes, it is also possible to achieve filters having different numbers of radiation transmissive wedge-shaped areas disposed in different configurations around center 356, again with the constraint of the value of β. To simplify the drawings, the electrical connection between the voltage control 360 and only one of the sector electrodes is shown in FIGS. 10A and 10B. Instead of being in the shape of sectors of a circle, electrodes 354 can also be in the shape of triangles. Where electrodes 354 are shaped as isosceles triangles, the array of electrodes 354 arranged around center 356 has the shape of a polygon. Still other shapes for the array 354 are possible.

If the wedge angle β is chosen to be too small, this means that an inordinate amount of space must be devoted to the separation between adjacent sector electrodes to avoid electrical shorting. Too large a value for β means that the wedge angle α can only be changed by large increments. Preferably β is at least about 5°.

For the normal illumination beam, the polarization state of the beam does not, to first order, affect detection. For the oblique illumination beam, the polarization state of the beam can significantly affect detection sensitivity. Thus, for rough film inspection, it may be desirable to employ S polarized radiation, whereas for smooth surface inspection, S or P polarized radiation may be preferable. After the scattered radiation from the sample surface originating from each of the two channels have been detected, the results may be compared to yield information for distinguishing between particles and COPs. For example, the intensity of the scattered radiation originating from the oblique channel (e.g., in ppm) may be plotted against that originating from the normal channel, and the plot is analyzed. Or a ratio between the two intensities is obtained for each of one or more locations on the sample surface. Such operations may be performed by a processor 400 in FIGS. 2A, 2B, 4, 5A, 5B.

While the invention has been described by reference to a normal and an oblique illumination beam, it will be understood that the normal illumination beam may be replaced by one that is not exactly normal to the surface, while retaining most of the advantages of the invention described above. Thus, such beam may be at a small angle to the normal direction, where the small angle is no more than 10° to the normal direction.

While the invention has been described above by reference to various embodiments, it will be understood that changes and modifications may be made without departing from the scope of the invention, which is to be defined only by the appended claims and their equivalents. For example, while only two illuminating beams or paths are shown in FIGS. 2A, 2B, 4, 5A, 5B, it will be understood that three or more illuminating beams or paths may be employed and are within the scope of the invention.

What is claimed is:

1. An optical system for detecting anomalies of a sample, comprising:

focusing optics directing and focusing at least one beam of radiation along a path onto a spot on a surface of the sample;

a first detector;

collection optics receiving scattered radiation from the sample surface and originating from the at least one beam and focusing the scattered radiation to said first detector for sensing anomalies;

a second, position sensitive, detector detecting a specular reflection of said at least one beam in order to detect any change in height of the surface at the spot; and a device altering the path of the at least one beam in response to the detected change in height of the surface at the spot to reduce position error of the spot caused by change in height of the surface at the spot, wherein said device alters said path without substantially moving the focusing optics.

2. The system of claim 1, said device comprising an optical element, and means for moving the optical element.

3. The system of claim 2, said focusing optics comprising three lenses focusing a beam from the optical element to the sample surface.

4. The system of claim 2, said second detector providing a position error signal indicating height of the sample surface at the spot, said device comprising:

means for providing a control signal having an amplitude equal to about half that of the position error signal; and a transducer rotating the optical element by an amount proportional to the amplitude of the control signal.

5. The system of claim 4, said providing means comprising a controller.

6. The system of claim 2, said focusing optics comprising a lens focusing a beam from the optical element to the sample surface.

7. The system of claim 2, said focusing optics comprising a single lens focusing a beam from the optical element to the sample surface.

8. The system of claim 7, said second detector providing a position error signal indicating height of the sample surface at the spot, said device comprising:

means for providing a control signal having an amplitude equal to about half that of the position error signal; and a transducer rotating the optical element by an amount proportional to the amplitude of the control signal.

9. The system of claim 2, said optical element located at a focal point of the focusing optics.

10. The system of claim 2, said optical element comprising a mirror.

11. An optical method for detecting anomalies of a sample, comprising:

focusing at least one beam of radiation along a path onto a spot on a surface of the sample by means of focusing optics;

receiving scattered radiation from the sample surface and originating from the at least one beam and focusing the scattered radiation to a first detector for sensing anomalies;

detecting a specular reflection of said at least one beam in order to detect any change in height of the surface at the spot; and altering the path of the at least one beam in response to the detected change in height of the surface at the spot to reduce position error of the spot caused by change in height of the surface at the spot, wherein said altering said path does not substantially move the focusing optics.

12. The method of claim 11, wherein said focusing focuses a beam of radiation from an optical element to the sample, wherein said altering includes moving the optical element.

13. The method of claim 12, further comprising locating said optical element at a focal point of the focusing optics.

14. The method of claim 12, wherein said focusing focuses a beam of radiation from a mirror to the sample.

15. The system of claim 11, said specular reflection detection providing a position signal indicating height of the sample surface at the spot, said altering comprising:

providing a control signal having an amplitude equal to about half that of the position error signal; and rotating the optical element by an amount proportional to the amplitude of the control signal.

16. An optical system for detecting anomalies of a sample, comprising:

illumination optics directing and focusing at least one beam of radiation along a path onto a spot on a surface of the sample, illuminating optics comprising focusing optics and an optical component;

a first detector;

collection optics receiving scattered radiation from the sample surface and originating from the at least one beam and focusing the scattered radiation to said first detector for sensing anomalies;

a second, position sensitive, detector detecting a specular reflection of said at least one beam in order to detect any change in height of the surface at the spot; and a device altering the path of the at least one beam in response to the detected change in height of the surface of he spot to reduce position error of the spot caused by change in height of the surface at the spot, wherein said device alters said path by moving said optical component.

17. An optical method for detecting anomalies of a sample, comprising:

directing and focusing at least one beam of radiation along path onto a spot on a surface of the sample means of focusing optics and an optical element;

receiving the scattered radiation from the sample surface and originating from the at least one beam and focusing the scattered radiation to a first detector for sensing anomalies;

detecting a specular reflection of said at least one beam in order to detect any change in height of the surface at the spot; and altering the path of the at least one beam in response to the detected change in height of the surface at the spot to reduce position error of the spot caused by change in height of the surface at the spot, wherein said altering alters the path by moving said optical component.

* * * * *